United States Patent [19]

Marsoner et al.

[11] 4,351,798
[45] Sep. 28, 1982

[54] ANALYZING APPARATUS FOR LIQUID SAMPLES

[75] Inventors: Hermann Marsoner; Helmut List, both of Graz; Erich Kleinhappl, Kumberg, all of Austria

[73] Assignee: Hans List, Graz, Austria

[21] Appl. No.: 233,574

[22] Filed: Feb. 11, 1981

[30] Foreign Application Priority Data

Feb. 12, 1980 [AT] Austria ................................. 748/80
Aug. 14, 1980 [AT] Austria ................................. 4196/80

[51] Int. Cl.$^3$ ........................ G01N 1/14; G01N 35/06
[52] U.S. Cl. ................................. 422/63; 73/864.85; 422/103
[58] Field of Search ............... 422/63, 81, 100, 103; 141/130; 73/864.84, 864.85

[56] References Cited

U.S. PATENT DOCUMENTS

| | | | |
|---|---|---|---|
| 3,449,081 | 6/1969 | Hughes | 422/100 X |
| 3,734,127 | 5/1973 | Williams et al. | 422/103 |
| 4,118,195 | 10/1978 | Beach | 422/100 X |
| 4,276,260 | 6/1981 | Drabal et al. | 422/100 X |
| 4,298,575 | 11/1981 | Berglund | 422/100 X |

Primary Examiner—Ronald E. Serwin
Attorney, Agent, or Firm—Watson, Cole, Grindle & Watson

[57] ABSTRACT

An analyzing apparatus for measuring samples of a liquid has feeding means for feeding the samples contained in sample containers to a subsequent sample conduit, the feeding means having a substantially funnel shaped filling mouth serving for fastening sample containers of very different shapes, such as syringes, pipettes or capillary tubes, and the dimensions of the outlet opening thereof varying within wide limits. A cleaning device can be used, which has a washing body which during the cleaning operation, together with the funnel shaped filling mouth, defines an annular gap adapted to match the form of the filling mouth and is providable with a cleaning medium.

To ascertain the presence and opening diameter category of a sample container and to automatically adjust the appropriate operating condition of the analyzing device, at a distance before the sample feeding inlet, an oscillation emitter and, with respect to the center of the sample feeding inlet, diametrically opposite the emitter and at a distance from the center of the sample feeding inlet, at least two identical detectors for the emitter oscillations are arranged, whereby according to the respective number of detectors which, after insertion of a certain sample container in the sample feeding inlet, will receive a signal or not, depending on the dimensions of the sample container present between emitter and detector, the adequate operating condition of the analyzing device is automatically adjustable.

9 Claims, 7 Drawing Figures

ANALYZING APPARATUS FOR LIQUID SAMPLES

BACKGROUND OF THE INVENTION

The present invention relates to an analysing apparatus for measuring samples of a liquid, the apparatus having feeding means for feeding the samples contained in sample containers through a sample conduit.

DESCRIPTION OF THE PRIOR ART

Such an analysing apparatus is disclosed in German Laid Open Print No. 2 521 061 and includes a sample feeding means in the form of an elongated tubelike sample probe through which the samples to be measured may be sucked into the subsequent sample conduit or into an analysing chamber incorporated in the conduit. The tubelike sample probe for taking up the sample protrudes skewly from the device and dips, with its point, in the sample container actually used. Apart from the susceptibility of the thin protruding sample probe to mechanical damage, the manner of taking up the sample of the known device presents itself an essential disadvantage as, in any case, a sample container is required having a relatively large opening for the passage of the sample probe and as, because of an easy handling of the sample containers and/or a simple operation of the analysing device, a relatively large quantity of the sample must be present.

SUMMARY OF THE INVENTION

It is an object of the present invention to improve upon the aforedescribed analysing apparatus in such a manner that the noted disadvantages of the known apparatus will be avoided and that especially the sample feeding means will be improved in such a way that different sample containers can be used, that small sample quantities will be sufficient, and that the risk of a mechanical damage of the sample feeding means itself will be avoided.

According to the invention this object is achieved in that the feeding means for feeding the sample has a substantially funnel shaped filling mouth serving for fastening the sample container. The funnel shaped filling mouth will ensure that sample containers of very different shapes, such as syringes, pipettes or capillary tubes, and dimensions of their outlet opening varying within wide limits can be used, and, further, that it may be possible to feed the sample directly into the sample conduit by hand, e.g., by means of micro-pipettes or syringes, and that—this is of special advantage for operating the apparatus—there are no mechanically susceptible parts present, the damage of which during the frequent feeding of samples would immediately lead to a failure of the apparatus.

According to a further embodiment of the invention the filling mouth is made of a resilient material, preferably a transparent plastics material, and is in the form of a filling means separately insertable in the sample feeding means sealing the subsequent sample conduit by its inherent resilient bias. Smaller sample containers, e.g., capillary glass tubes, can be urged into the resilient funnel of the filling mouth so that they remain in the fixed position without any support; the operation of the apparatus is such simplified. Additionally the resilient filling mouth itself provides for an easy seal between sample container and sample feeding means the seal of the separately inserted filling part in the sample feeding device being effected by a suitable shape and/or suitable dimensions of the filling part providing for a resilient bias against the directly adjacent part of the sample feeding means. This filling part is easy and cheap to manufacture so that it can readily be replaced by a new part, e.g., after damage of gross contamination.

According to a still further embodiment of the invention having a transparent filling part a light fitting is arranged below the transparent filling mouth, the light fitting indicating various operating conditions of the analysing apparatus. Thereby, not only the feeding opening is marked in a manner facilitating the operation of the analysing apparatus, but there is also a possibility to indicate different operating conditions of the analysing apparatus such as sample input or sample processing.

With an analysing apparatus having a cleaning device for removing remainders of the samples from the sample feeding means and the successive sample conduit the invention provides a further convenient embodiment wherein the cleaning device has a washing body which during the cleaning operation, together with the funnel shaped filling mouth, defines a annular gap adapted to match the form of the filling mouth and being provided with a cleaning medium from the inlet. A thorough cleaning of the sample feeding means as well as of the subsequent sample conduit after working up each sample is of essential importance to prevent falsifications of the results of measurements which, especially in case of small quantities of substances to be proved, would take a marked effect. For this purpose the device known from the aforementioned German Laid Open Print No. 2 521 061 has a cleaning device which permits cleaning of the sample probe by dipping it in a washing liquid after the sample has been received and forwarded. The washing liquid is fed into the container in which the probe dips in such a way that the pure washing liquid which is sucked through the sample probe and the sample conduit is followed by a mixture of washing liquid and air which should enhance the cleaning effect. Contrary to this relatively expensive construction of the washing liquid supply, the present invention discloses a mere washing body which, during the cleaning operation, constitutes an annular gap along the funnel shaped filling mouth which annular gap is fed with the cleaning medium. Due to the annular gap, relatively high flow rates occur during the passage of the cleaning medium through the gap and a marked cleaning effect is achieved, and, according to a further feature of the invention, it is particularly convenient to feed the annular gap between washing body and filling mouth with washing liquid at the beginning of the cleaning operation and then with air for drying. The annular gap between washing body and filling mouth has a particularly favorable effect on the successive air drying as an accumulation of droplets in the region of the funnel can be prevented safely due to the increase of the flow rate.

According to another feature of the invention the part of the washing body co-operating with the filling mouth is adapted substantially to the shape of the filling mouth in this region and is arranged within the cleaning device in a manner that an annular gap is formed between its basis and the cleaning device which gap is connected to the inlet for the cleaning medium. By providing the annular gap at the basis of the washing body the shape of which is adapted to the shape of the filling funnel a steady supply of washing liquid and drying air, respectively, to the annular gap between filling funnel and washing body is ensured, which results in a uniform cleaning and drying effect over the whole circumference of the filling mouth.

In this connection it is advantageous, too, to seal the annular gap between washing body and filling mouth against the surrounding exterior during the cleaning operation by a sealing part of the cleaning device contacting the sample feeding means. These features, in connection with the provision of the annular gap between washing body and filling mouth, ensure that a minimum amount of cleaning medium will be sufficient and that the rest of the analysing apparatus will not come into contact with the cleaning medium.

In order to facilitate the operation of the analysing apparatus it is especially convenient according to another feature of the invention to arrange the cleaning device on a supporting arm pivotally mounted on the analysing apparatus which supporting arm is movable above the filling mouth at the beginning of the cleaning operation so that the washing body will be coaxially aligned with the filling mouth, the supporting arm urging the cleaning device into a sealing contact with the filling mouth of the sample feeding means on being lowered in the direction of the axis of the filling mouth. The pivoted supporting arm allows an exact positioning of the cleaning device and and the washing body, respectively, to be repeated at any time so that, in any case, the annular distance between washing body and filling mouth will be ensured. In this connection it is of particular advantage, when the operation of the supporting arm, controlled by the analysing device, is effected automatically, preferably by electromechanical operating means; in this case, e.g., measurements in series with very short intervals can be performed without the risk of forgetting the cleaning of the sample feeding means and the subsequent sample conduit.

In the practice of analysing shows the user will expect the sample to be automatically sucked from the capillary glass tube into the analysing apparatus by a suction mechanism, whereas, in the case of samples contained in syringes which can be of different capacities, it will be expected that any quantity of the sample contained in a syringe, though exceeding a minimum quantity, can be injected into the apparatus. These two kinds of sample feeding require different operating conditions which usually will be selected by means of a selector prior to feeding the sample. This mode of operation has the disadvantage that pre-adjustment by operators frequently causes errors, which will result in troubles on feeding the samples.

According to a further embodiment of the invention such disadvantages are prevented by a device characterized in that, at a distance before the sample feeding inlet, an emitter of electromechanical oscillations, or light or sound oscillations, preferably infra-red or supersonic oscillations, is arranged and that, with respect to the center of the sample feeding inlet, diametrically opposite the emitter and at a distance from the center of the sample feeding inlet there are arranged, juxtaposed, at least two identical detectors for the emitter oscillations, whereby, according to the respective number of detectors which, after insertion of a certain sample container in the sample feeding inlet, will receive a signal or not, depending on the dimensions of the sample container present between emitter and detectors, the adequate operating condition of the analysing device is automatically adjustable. Such a device at first will deliver an information regarding the presence of a sample container such as a capillary glass tube or usual syringe and then will automatically adjust the appropriate operating condition of the analysing device.

According to a further feature of the invention a plurality of detectors of smallest dimensions is arranged in series in order to increase the safety of identifying more than two different types of sample containers.

DESCRIPTION OF THE DRAWINGS

The invention will be further illustrated with reference to the accompanying drawings showing an embodiment of the invention.

DESCRIPTION OF THE PREFERRED EMBODIMENTS

Figure 1:
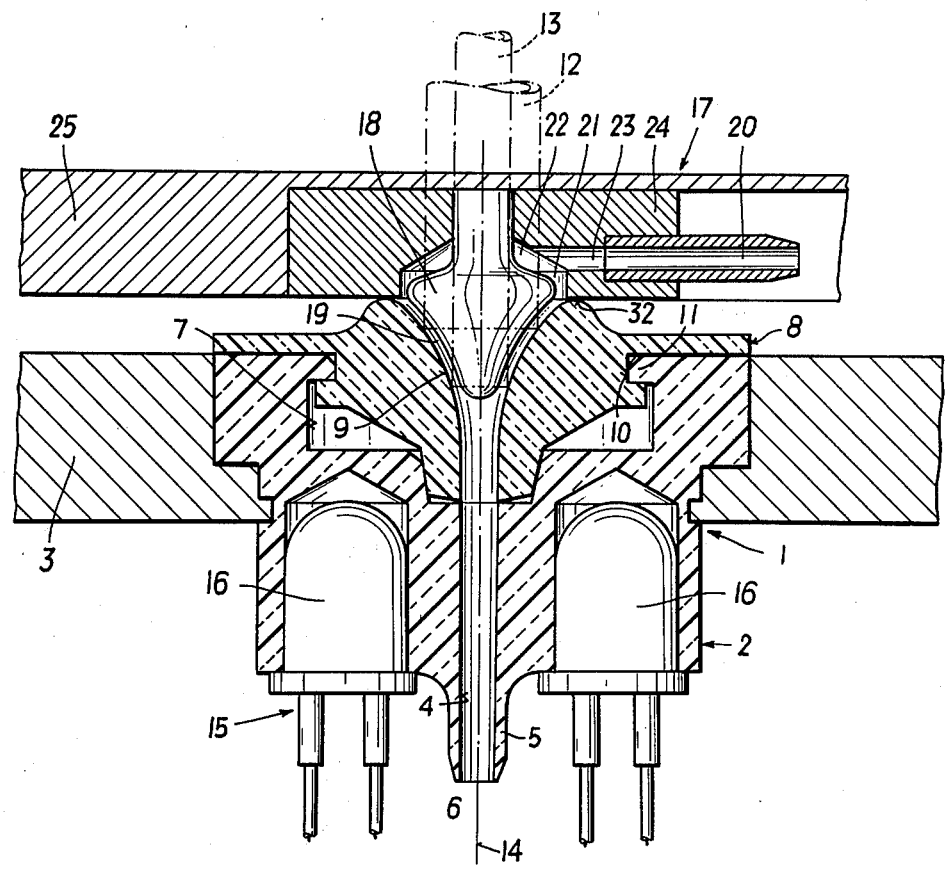
FIG. 1 is a sectional view of the analysing apparatus according to the invention in the region of the sample feeding means and at an enlarged scale.

According to FIG. 1 the sample feeding means 1 has a support 2 inserted and fixed in the cover plate 3 of an analysing apparatus not shown in detail. In the embodiment shown the support 2 is made of a transparent, rigid material such as plastics, it is cylindrically shaped and has a central bore 4 which is part of a sample conduit 6 extended a tube (not shown) which can be mounted on nipple 5.

As shown in the drawing, the top of the support 2 is provided with a recess 7, able for the reception of a separate insertable filling means 8 comprising an insert of resilient material, preferably plastics material. The filling means 8 has a concentric and substantially funnel shaped filling mouth 9 which, adjacent the bore 4 of the support 2, has a diameter essentially corresponding to that of the bore of the sample conduit 6. The bottom portion of the insert forming the filling means 8 is so shaped, that, when mounted within recess of as its annular groove 10 engages an annular projection 11 of support 2, it forms a seal against the sample conduit 6 by reason of its inherent bias.

The funnel shaped filling mouth 9 of the filling means 8 has a shape to accommodate use of sample containers of various connection or outlet diameters. In FIG. 1 by way of example the front part of a plastics syringe 12 shown in phantom outline will, because of its larger diameter, contact the filling mouth 9 sooner than, e.g., a capillary glass tube 13 (likewise shown in phantom outline) when being placed in the sample feeding means 1. By exerting a light pressure in the direction of the axis 14 of the sample conduit 6 the syringe 12 as well as the capillary tube 13 can be sealed against the resilient filling means 8 in a very simple manner, the capillary tube 13 shown being capable of already advancing so far in the filling mouth 9 that it will be supported by the filling mouth 9 during reception of the sample.

The transparency of the support 2 as well as of the filling means 8, which is easily replaceably supported in the former, allows the provision of a light fitting 15 which comprises a plurality of illuminators 16 mounted in the support 2 and which indicates various operating conditions of the analysing apparatus directly on the sample feeding device in a manner comfortable to the operator.

A special problem of such analysing apparatus, particularly on analysing biological fluids such as blood, consists in that all the parts of the analysing apparatus which come in contact with the sample must be cleaned intensively and thoroughly after each single analysis in order not to affect any subsequent measurement as well as in order to meet the hygienic requirements. For this purpose, according to FIG. 1, a cleaning device 17 is provided having a washing body 18 which during the cleaning operation—as shown in FIG. 1—together with the funnel shaped filling mouth 9 defines an annular gap 19 adapted to the form of the filling mouth which gap can receive a cleaning medium via an inlet 20 which may be connected (not shown), e.g., to a rubber hose. The part of the washing body 18 cooperating with the filling mouth 9 is adapted to the shape of the filling mouth in the respective region and is arranged in the cleaning device 17 so that an annular gap 21 is formed between its base and the cleaning device which annular gap is supplied with cleaning medium from a space 22 which communicates with the inlet 20 via a bore 23. The washing body 18 has the form of an element separately mounted in an insert 24 which, carrying also the inlet 20, is mounted on a supporting arm 25.

Figure 2:
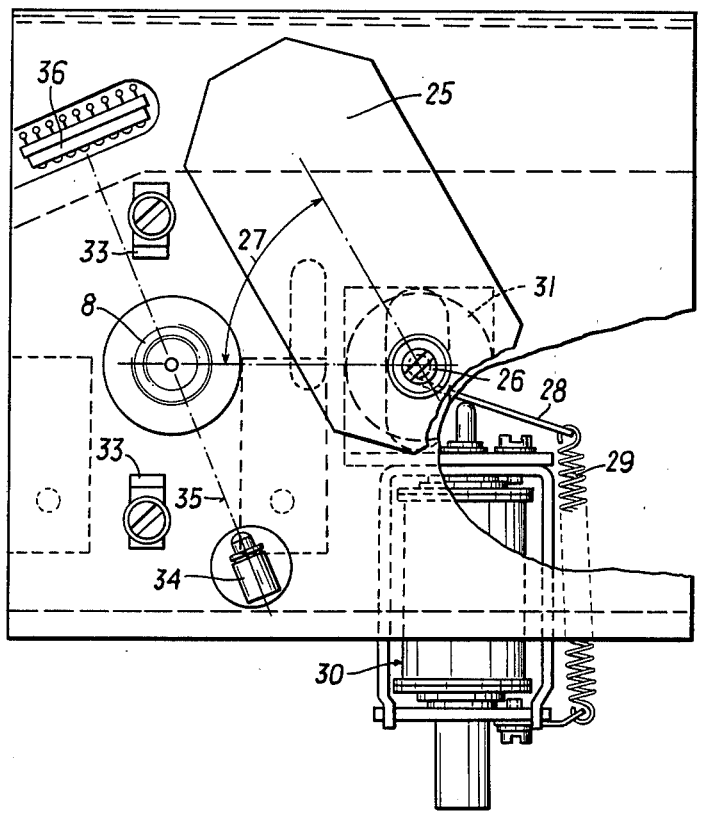
FIG. 2 is a full-scale top plan view of the analysing apparatus in the region of the sample feeding means and the cleaning device.

As shown in FIG. 2 the supporting arm 25 is movable relative to the filling means 8 about an axis 26 over an angle 27, the movement being facilitated by a swivelling lever 28 which is biased by a spring 29 and is operated by an electromagnet 30 controlled by the analysing apparatus. By means of a further electromagnet 31 the axis 26 is shiftable in a longitudinal direction with the movement being controlled by the analysing apparatus so that the suppporting arm 25 after completion of sample feeding is first turned about the angle 27 over the filling means and then is moved into the position relative to the sample feeding means 1 shown in FIG. 1 by means of the electromagnet 31. At the beginning of the cleaning operation the annular gap 19 between washing body and filling mouth 9 is fed with washing liquid via inlet 20, bore 23, space 22 and annular gap 21, the washing liquid having a high flow rate due to the annular gap 19 sweeping along any contamination present in the region of the filling mouth 9 and the subsequent sample conduit 6. Due to the pulling action of the electromagnet 31 mentioned in connection with FIG. 2 the upper edge 32 of the filling mouth 9 lies sealingly against the insert 24 of the cleaning device 17 so that washing liquid cannot escape during the cleaning operation. After the sample conduit 6 has been washed air for drying is sucked via inlet 20 which air due to the increase of its flow rate in the region of the annular gap dries the said gap completely clean without leaving any residue. Then the supporting arm 25 is raised from the filling means 8 along the axis 26 and about the angle 27 returned to its rest position. The analysing apparatus is then prepared again for feeding a sample which can be indicated, e.g., by means of the light fitting 15.

During the cleaning operation the supporting arm 25 turned over the sample feeding means is fixed by exactly adjusted stops 33 so as to maintain uniformity of the annular gap 19.

FIG. 2 additionally shows an arrangement permitting identification of a characteristic diameter of the fastened sample container which influences the performance of the analysis depending on the type of sample container used. For this purpose an emitter 34 is provided which, directed toward the axis of the filling means 8 (direction 35), emits infra-red light, ultrasonic oscillations or the like. By means of a battery 36 of receivers it is possible to determine the extension of the shadow of a sample container fastener on the filling means 8 and to use the dimension of the shadow, which is directly proportional to the dimension of the sample container, for further influencing the performance of the analysis.

Figure 3:
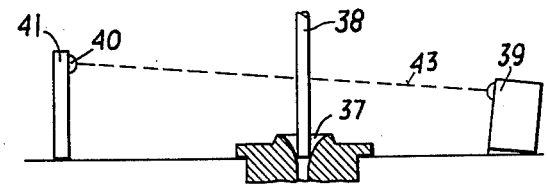
FIG. 3 is a side elevation of the sample feeding inlet showing a capillary glass tube fixed between emitter and detectors.
Figure 5:
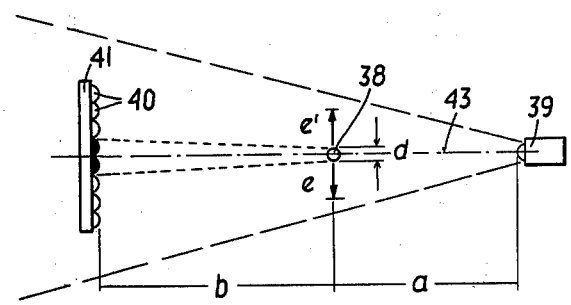
FIG. 5 shows the identification of a sample containing capillary tube within the range of detection of the detectors.

FIG. 3 shows a section through the sample feeding opening 37 of an analysing apparatus according to the invention (not shown) with tightly inserted capillary tube 38 which is situated within the raybeam 43 of the emitter 39 diametrically opposite to which a series 41 of detectors consisting of eight single detectors 40 is arranged. FIG. 5 shows the same arrangement in a top plan view of the capillary tube 38 containing the sample. It is to be seen that the distances a and b of emitter and series 41 of detectors, respectively, are so dimensioned that for the standardized diameter d of a capillary tube 38 one or two single detectors 40 of the detector series 41 each are switched off within the detected region e-e'.

The single detectors 48 are represented by segments of circles; the shaded detectors are fully blackened. Shading of one to two detectors results in the sum information that a sample container is present in the sample feeding opening and that the sample container is a capillary tube.

Figure 4:
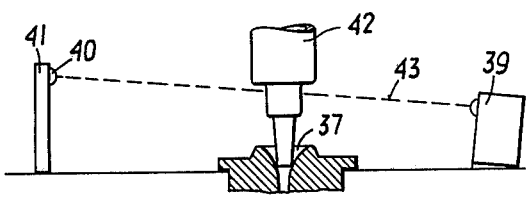
FIG. 4 is a side elevation of the sample feeding inlet showing a syringe fixed between emitter and detectors.
Figure 6:
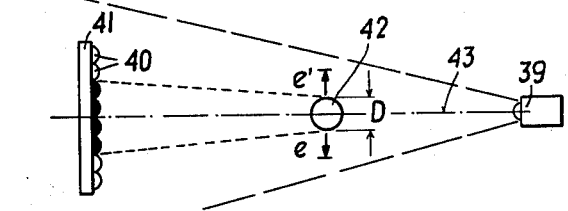
FIG. 6 shows the identification of a syringe within the range of detection of the detectors.

Analogously FIGS. 4 and 6 show a portion 42 of a syringe held at the sample feeding opening and having the diameter D as well as the shaded image on the detectors within the detected region e-e'. In the embodiment shown shading of more than two detectors results in the information that a sample container having the shape of a syringe is present in the sample feeding opening 37.

The drawings illustrate a convenient embodiment of the invention using a source of infra-red light as an emitter and a series of eight photo transistors as a detector. The shown number of eight detectors is not obligatory. It can be shown that the diameters d of capillary tubes (preferably 1.0 to 1.5 mm) can be sufficiently distinguished over diameters D of syringes (about 3 6 mm) using a minimum of two detectors. The arrangement of a plurality of detectors of smallest dimensions in a series has advantages in view to a safe identification, if the position of the sample container should vary in the detected region e-e'. Additionally, such an arrangement can be used for the identification of more than two categories of diameters.

Figure 7:
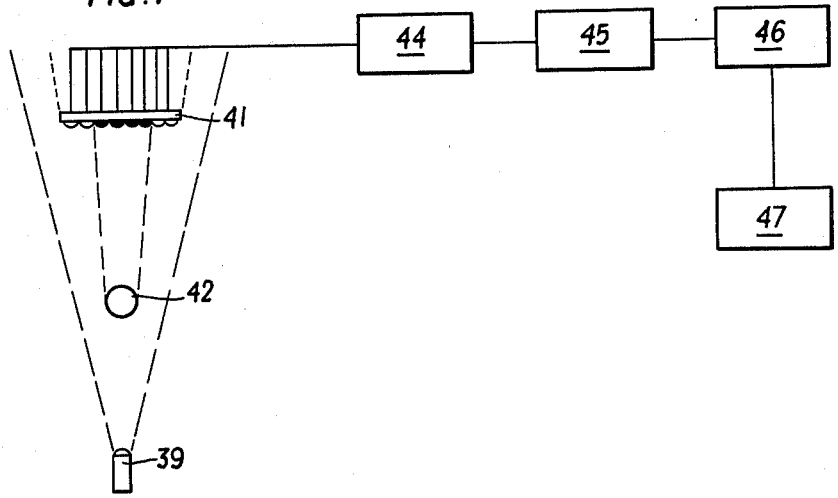
FIG. 7 shows the complete arrangement diagrammatically.

The function of the device will be illustrated with reference to FIG. 7. The sample container 42 present in the path of rays of the emitter 39 causes two detectors each at the ends of the detector series 41 comprising eight detectors to be lighted and the inner four detectors not to be lighted. The number of detectors which are lighted or not lighted will be determined by a signal processing unit 44. By criteria set in the logic element 45 a statement is derived therefrom concerning the category of diameters the sample container 42 present at the inlet of the analysing apparatus belongs to. Accordingly, the sample guiding means in the analysing apparatus 47 will be switched by means of the control unit 46 so that a sample contained, e.g., in a capillary tube (a sample container of a small diameter category) will be sucked into the analysing apparatus by means of a suction device or that, in the case of a sample present in a syringe (large diameter category), the sample paths are connected in a way that the sample can be injected into the analysing apparatus.

I claim:

1. Feeding means for the feeding of liquid samples from sample containers into an analyzing apparatus for measuring the samples, the feeding means comprising a support having a sample conduit and an upwardly open substantially funnel-shaped filling mouth to accommodate use of the sample containers having various matching-part outlet diameters, said filling mouth being of resilient material and being aligned with said sample conduit through which the liquid samples are fed.

2. The feeding means according to claim 1, including filling means in the form of an insert of transparent plastic material, said insert containing said filling mouth and engaging said support for resiliently sealing against said sample conduit under its own resiliency.

3. The feeding means according to claim 2, further including a light fitting mounted in said support below said filling mouth for indicating various operating conditions of the analyzing apparatus directly on the feeding means.

4. The feeding means according to claim 1, further including a cleaning device mounted over said filling mouth and having a washing body having a profile matching that of said filling mouth, said washing body extending into said mouth and forming an annular gap therewith, and said device including an inlet communicating with said gap for introducing a cleaning medium into said mouth and said conduit for the cleaning of same, followed by drying air for the drying of same.

5. The feeding means according to claim 4, wherein said device sealingly engages an outer end of said mouth for to avoid leakage between said inlet and said gap.

6. The feeding means according to claim 4, wherein said cleaning device includes a support arm pivotally mounted on the apparatus for movement of said device into an aligned position between said washing body and said filling mouth, and said arm being also mounted for axial movement in the direction of said conduit for sealingly engaging an outer end of said mouth.

7. The feeding means according to claim 6, wherein electromechanical operating elements are provided for pivotally and axially moving said arm.

8. The feeding means according to claim 1, further comprising a device for detecting each of the outlet diameters when supported at said mouth comprising, an oscillation emitter and at least two juxtaposed and identical detectors for receiving signals from said emitter, said emitter and said detectors lying on opposite sides of said outlet diameter at spaced distances therefrom, whereby a predetermined number of said detectors depending on the diameter size of the sample container will receive no signals from said emitter as they are blocked by the container, and the remainder of said detectors will receive said signals, said device including a further signal as said remainder of said detectors receive said emitter signals to facilitate automatic adjustment of the operating condition of the analyzer.

9. The feeding means according to claim 8, wherein said detectors are arranged in series.

* * * * *